US009725345B2

(12) United States Patent
Garrido Fernandez et al.

(10) Patent No.: US 9,725,345 B2
(45) Date of Patent: Aug. 8, 2017

(54) INTEGRATED SYSTEM OF A METHANOGENIC ANAEROBIC REACTOR AND MEMBRANE BIOREACTOR FOR THE ELIMINATION OF ORGANIC MATERIAL AND NITROGEN FROM WASTEWATER

(71) Applicant: UNIVERSIDADE DE SANTIAGO DE COMPOSTELA, Santiago de Compostela (ES)

(72) Inventors: Juan Manuel Garrido Fernandez, Santiago de Compostela (ES); Dagmara Buntner, Santiago de Compostela (ES); Alberto Sanchez Sanchez, Santiago de Compostela (ES); Juan Manuel Lema Rodicio, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 31 days.

(21) Appl. No.: 14/765,055

(22) PCT Filed: Jan. 30, 2014

(86) PCT No.: PCT/ES2014/070067
§ 371 (c)(1),
(2) Date: Jul. 31, 2015

(87) PCT Pub. No.: WO2014/118416
PCT Pub. Date: Aug. 7, 2014

(65) Prior Publication Data
US 2015/0368131 A1 Dec. 24, 2015

(30) Foreign Application Priority Data
Feb. 1, 2013 (ES) .................................. 201330118

(51) Int. Cl.
*C02F 3/30* (2006.01)
*C02F 3/10* (2006.01)
(Continued)

(52) U.S. Cl.
CPC ............ *C02F 3/301* (2013.01); *C02F 3/1273* (2013.01); *C02F 3/302* (2013.01); *C02F 3/305* (2013.01);
(Continued)

(58) Field of Classification Search
CPC ...... C02F 3/301; C02F 3/1273; C02F 3/2806; C02F 3/2846; C02F 3/302; C02F 3/305;
(Continued)

(56) References Cited

U.S. PATENT DOCUMENTS

| | | | |
|---|---|---|---|
| 2004/0031734 A1* | 2/2004 | Chen | C02F 3/2806 210/150 |
| 2005/0045557 A1* | 3/2005 | Daigger | C02F 3/1215 210/605 |

(Continued)

FOREIGN PATENT DOCUMENTS

| | | |
|---|---|---|
| ES | 2 385 002 A1 | 7/2012 |
| GB | 2 167 055 A | 5/1986 |

(Continued)

OTHER PUBLICATIONS

Machine-generated English translation of ES 2385002, generated on Oct. 26, 2016.*
(Continued)

*Primary Examiner* — Fred Prince
(74) *Attorney, Agent, or Firm* — Sughrue Mion, PLLC

(57) ABSTRACT

Integrated methanogenic anaerobic reactor and membrane bioreactor, and method for eliminating organic matter and nitrogen in urban or industrial wastewater, preferably with COD concentrations between 150 and 5000 mg/L and where
(Continued)

the eliminations of total nitrogen that occur are between 15 and 50 mg/L, at temperatures above 15° C. The wastewater treatment takes place thanks to three stages of treatment: methanogenic anaerobic stage, anoxic stage with biofilms and suspended biomass and aerobic filtration stage with biofilms and suspended biomass.

18 Claims, 2 Drawing Sheets

(51) Int. Cl.
    *C02F 3/12*     (2006.01)
    *C02F 3/28*     (2006.01)
    *C12M 1/00*     (2006.01)
    *C12M 1/06*     (2006.01)
    *C02F 101/16*     (2006.01)
    *C02F 3/08*     (2006.01)

(52) U.S. Cl.
    CPC ............ *C12M 23/38* (2013.01); *C12M 27/02* (2013.01); *C12M 29/00* (2013.01); *C12M 29/04* (2013.01); *C12M 29/18* (2013.01); *C02F 3/085* (2013.01); *C02F 3/10* (2013.01); *C02F 3/286* (2013.01); *C02F 3/2806* (2013.01); *C02F 3/2846* (2013.01); *C02F 2101/16* (2013.01); *C02F 2203/006* (2013.01); *C02F 2209/08* (2013.01); *C02F 2209/16* (2013.01); *Y02W 10/15* (2015.05)

(58) Field of Classification Search
    CPC ............ C02F 2101/16; C02F 2203/006; C02F 2209/08; C02F 2209/16; C02F 3/085; C02F 3/10; C02F 3/286; C12M 23/38; C12M 27/02; C12M 29/00; C12M 29/04; C12M 29/18; Y02W 10/15
    USPC ....... 210/603, 605, 612, 615, 616, 617, 630, 210/903
    See application file for complete search history.

(56) References Cited

U.S. PATENT DOCUMENTS

2005/0109694 A1    5/2005  You et al.
2012/0006744 A1*  1/2012  Phattaranawik ........ C02F 3/301
                                          210/605

FOREIGN PATENT DOCUMENTS

JP        2009-148714 A    7/2009
WO     2004/011377 A2    2/2004

OTHER PUBLICATIONS

International Search Report of PCT/ES2014/070067 dated Mar. 21, 2014.

* cited by examiner

INTEGRATED SYSTEM OF A METHANOGENIC ANAEROBIC REACTOR AND MEMBRANE BIOREACTOR FOR THE ELIMINATION OF ORGANIC MATERIAL AND NITROGEN FROM WASTEWATER

CROSS REFERENCE TO RELATED APPLICATIONS

This is a National Stage of International Application No. PCT/ES2014/070067 filed Jan. 30, 2014, claiming priority based on Spanish Patent Application No. 201330118 filed Feb. 1, 2013, the contents of all of which are incorporated herein by reference in their entirety.

TECHNICAL FIELD OF THE INVENTION

The present invention proposes an Integrated System comprising an anaerobic methanogenic reactor and membrane bioreactor (SIAM), especially designed for the removal of organic matter and nitrogen in urban or industrial wastewater using an integrated bioreactor system that generates lower sludge production, lower energy consumption, and in which a final effluent is obtained that is free of suspended solids and low concentration of total nitrogen and organic matter.

The present invention combines the advantages of anaerobic biological systems, low sludge production and generation of a usable biogas, of aerobic systems, low Chemical Oxygen Demand (COD) of the treated effluent, at ambient temperature, and of membrane filtration systems, high effluent quality with very low concentrations of suspended solids and microorganisms. The system and method allow for the removal of nitrogen from wastewater using methane as a source of dissolved carbon present in the effluent of the methanogenic reactor thus reducing the emissions of one greenhouse gas, methane, present in the effluent of methanogenic bioreactors. The integrated system is particularly suitable for the treatment of urban and industrial wastewater with low or moderate concentrations of organic matter (between 150 and 5,000 mg/L COD), allowing a reduction of the total nitrogen in the treated water, usually between 15 and 50 mg/L in order to facilitate the direct discharge of the water or allow it to be reused for irrigation or industrial processes.

STATE OF THE ART

An Integrated System is proposed comprising an anaerobic methanogenic reactor and a membrane bioreactor (SIAM) that results in the improvement of patent application ES2385002-A1 for three-stage methanogenic, aerobic and filter bioreactor recommended for the removal of organic matter, suspended solids and microorganisms in treated wastewater, but that did not achieve an appreciable elimination of total nitrogen in the wastewater, and other limitations of the prior art.

The objective of this invention is to take advantage of the methane dissolved naturally in the effluent from the anaerobic methanogenic stage, in order to remove part of the total nitrogen in the purified wastewater. Thus two positive environmental objectives are achieved, removing nitrogen compounds from the wastewater while reducing emissions of methane, a highly potent greenhouse gas, greatly improving the environmental performance of the facilities.

Accordingly, there follows a detailed review of the state of the art with regard to systems for the removal of nitrogen from wastewater in general and in particular the use of methanogenic systems for wastewater treatment and the potential use of methane as a source of carbon in the biological denitrification reaction.

Nitrogen Removal Processes

The biological treatment of nitrogen compounds in wastewater is performed through a sequence of steps in series, in the first stage of hydrolysis the organic nitrogen present in the wastewater is hydrolysed, thus releasing ammonium ion, in the second nitrification stage the ammonia nitrite or nitrate is oxidised and in the third denitrification stage, the nitrogen anions are reduced to nitrogen gas, typically using a carbon source as an electron donor.

Of the different configurations for the integral treatment of nitrogen and organic matter, the most attractive are those in which the oxidation of organic matter and the nitrification-denitrification are combined in a joint treatment process. In these processes the reactor is divided into two or more chambers, one without air (anoxic chambers) and other aerated (aerobic chambers). In the anoxic chamber the nitrite and nitrate is reduced to nitrogen gas, using the organic matter present in the residual water as the carbon source and in the aerobic chambers the oxidation of ammonium to nitrite and nitrate takes place, together with the oxidation of organic matter residue that had not been degraded in the anoxic chambers. The denitrification reaction allows a saving of oxygen by recovering some of the oxygen and alkalinity consumed in the oxidation of ammonia to nitrate (Metcalf & Eddy Inc. Wastewater Engineering: Treatment and Reuse, 4th Edition, 2003 McGraw Hill Ed.). In terms of technologies used it is common to use the activated sludge system and its multiple configurations or biofilm systems such as submerged biofilters (Metcalf & Eddy 2003 Inc. Wastewater Engineering: Treatment and Reuse, $4^{th}$ Edition, 2003 McGraw Hill Ed.). The amount of organic matter that is required for denitrifying the nitrite and nitrate ions is usually around 4 to 8 g-COD/g-N removed.

At low COD/N ratios the denitrification process is often limited by the presence of organic matter, being the usual practice to add an external source of organic matter (for example methanol or acetic acid), which increases the system operating costs (Isaacs S. H. and M. Henze, Wat. Res. 29(1), 77 (1995)). In these cases, wastewater with a low COD/N ratio, the use can be contemplated of bioreactors in which the removal of autotrophic nitrogen is promoted, encouraging the joint growth of nitro-oxidising bacteria, which will oxidise part of the ammonium to nitrite and of anammox bacteria that perform denitrification by using ammonium ions as electron donors and the nitrite as an electron acceptor; thus forming nitrogen gas in the absence of any organic carbon source An example of autotrophic nitrogen removal systems are Sharon-Anammox CANON and OLAND systems, (Li A. et al. Recent Patents on Engineering 2008, 2, 189-194), however, the use of systems based on autotrophic nitro-oxidising and anammox bacteria is limited to treating flows of wastewater with moderate to high concentrations of nitrogen compounds at temperatures near 35-37° C., making them difficult and complex to operate at temperatures below 20° C. (Strous et al., Appl. Environ. Microbiol, 65, 3248 (1999))

Anaerobic Methanogenic Wastewater Treatment

Anaerobic methanogenic processes have been widely used for the treatment of urban and industrial wastewater; these systems have a number of advantages such as lower power consumption, the possible energy recovery of the methane gas generated and reduced sludge production compared to aerobic biological treatment technologies. Anaerobic processes are widely used in countries with temperate or warm climates for the treatment of urban wastewater, at ambient temperature, or for the treatment of industrial wastewater with high concentrations of organic matter although with the bioreactor normally operating at temperatures of about 35-37° C. in mesophilic anaerobic systems or 55-60° C. in thermophilic anaerobic systems.

More noteworthy anaerobic treatment technologies developed in recent decades include the anaerobic filter (AF), upflow anaerobic sludge blanket reactors (UASB) or expanded granular sludge bed reactors (EGSB) (Speece, R E, Anaerobic Biotechnology for Industrial Wastewater, Archae Press, Nashville, Tenn. (1996)). Of these technologies only UASB reactors have had some success in the treatment of urban wastewater because of their simplicity and ease of operation.

The UASB (Upflow Anaerobic Sludge Blanket) reactor, developed in the 1970s in the Netherlands, is formed by a blanket of anaerobic sludge, which is located in the lower part of the system, and a gas-liquid-solid (GLS), separator located at top of the reactor. The sludge blanket at the bottom of the reactor is formed both by the accumulation of solids in suspension and microorganisms added in floccule and granulated form. The GLS separator allows much of the solids that are washed by the upstream of water and biogas to be recovered, collecting the biogas bubbles through a series of domes strategically located along the top of the system.

UASB technology provides a simple and effective way to reduce the presence of organic pollutants in urban wastewater, in warm or tropical regions where the wastewater has a temperature of 20° C. throughout the year. Its use has become popular in countries like India, Pakistan, China, Colombia, Brazil, Indonesia and Egypt. Some of the installed plants use the biogas generated to meet the energy demands of the Wastewater Treatment Plant (WWTP). This technology is not viable for the treatment of urban wastewater in countries with temperate or cold climates owing to low cell productivity, low activity of microorganisms and the possible loss of biomass through drag-out of the biomass generated in the final effluent (washing). Furthermore, the anaerobic treatment of urban wastewater with UASB systems is not usually recommended in countries with high environmental standards, for not meeting the discharge thresholds marked by the European Union in terms of COD, BOD5, TSS or TN (Directive 91/271/EEC concerning urban wastewater treatment).

Many of these problems are avoided by using membrane filtration systems as specified in the three-stage methanogenic, aerobic and membrane filter bioreactor invention for urban wastewater (application ES2385002-A1) which also allows a purified effluent to be obtained with very low concentrations of organic matter (in terms of COD, DBO5 or TSS) operating the membrane with higher yields than those normally associated with anaerobic membrane bioreactor systems (Sanchez et al., Wat. Res., 47, 1227 (2013)).

One of the main problems of anaerobic pre-treatments is the output of dissolved methane in the treated effluent these effluents have a high concentration of dissolved methane in equilibrium with the gas phase according to Henry's law or may even be slightly super-saturated relative to said gas phase. The solubility of methane in water depends on its partial pressure and temperature. As an example, it can be estimated that the dissolved methane in the effluent of an anaerobic stage can be between 21 and 25.5 mg/L, data calculated at temperatures of 17-25° C. and partial gas phase methane pressures of 0.75 to 0.8 atm.

The presence of dissolved methane represents a major environmental problem in terms of greenhouse gas emissions associated with wastewater treatment in methanogenic bioreactors. Methane has a global warming potential 25 times higher than carbon dioxide. For the treatment of urban wastewater, the methane dissolved in the effluent could be up to 50% of the total methane generated in the anaerobic system, with the remaining being present in the biogas generated. Dissolved methane is readily desorbed from effluents, either those discharged directly into the environment, or especially those post-treated in an aerobic bioreactor, significantly increasing the emission of greenhouse gases associated with the wastewater treatment. These problems could be avoided by using post-treatment technologies such as bio-filters or desorption columns associated with gas incinerators, but have problems associated with their low efficiency and high costs of operation (Scheutz C. et al., Waste Manag. Res., 27, 409, (2009)).

Use of Methane as a Carbon Source in the Biological Denitrification Reaction.

The biological denitrification of wastewater with a poor content of organic matter requires an external electron donor. Methane is an available and inexpensive electron donor for the denitrification of a wastewater after a methanogenic treatment. This reaction is possible in standard conditions from a thermodynamic point of view ($\Delta G^0 = -767$ kJ·mol$^{-1}$)

From the kinetic point of view, biological denitrification using methane as electron donor can occur in three ways:

1) Aerobic oxidation of methane coupled to denitrification. This takes place via a microbial consortium featuring the coexistence of aerobic methanotrophic bacteria that oxidize methane into various oxidation products and heterotrophic denitrifying bacteria that use said partial oxidation products as electron donors in the denitrification reaction. The theoretical stoichiometry of the process would be defined by the reaction (1).

$$5CH_4 + 5O_2 + 4NO_3^- + 4H^+ \rightarrow 2N_2 + 12H_2O + 5CO_2 \quad (1)$$

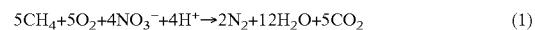

2) Aerobic oxidation of methane coupled to denitrification. The anoxic oxidation of methane would be carried out through a partnership of methanogenic archaea and sulphate-reducing bacteria that use nitrate instead of sulphate as an electron acceptor.

3) Direct methanotrophic denitrification. Anaerobic methane oxidation is carried out thanks to type NC10 bacteria that metabolise nitrite via nitric oxide to nitrogen gas without the need for association with archaea. These bacteria have been enriched in sequential reactors (Kampman et al., J. Hazard.) Mat., 227-228, 164 (2012)). The stoichiometry of the process would be defined by the reaction (2).

$$5CH_4 + 8NO_3^- + 8H^+ \rightarrow 5CO_2 + 4N_2 + 14H_2O \quad (2)$$

$$\Delta G^0 = -767 \text{ kJ·mol}^{-1}$$

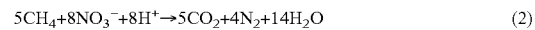

In the present invention Integrated System of Anaerobic methanogenic reactor and Membrane bioreactor, the dissolved methane present in the effluent will be used as a carbon source for denitrifying in the anoxic stage.

Improvements Obtained with the Present Invention

The present invention Integrated System of Anaerobic methanogenic reactor and Membrane bioreactor is an improvement over the prior art, in particular the three-stage methanogenic, aerobic and membrane filter bioreactor of patent application ES2385002-A1 for the biological treatment of urban or industrial wastewater with low or moderate concentrations of COD organic matter (between 150 and 5000 mg COD/L) and nitrogen, in which the organic contaminants must be removed from the wastewater at moderate temperatures, allowing the removal of 15 to 50 mg/L of total nitrogen.

One of the main features of the proposed biological reactor lies in properly combining the three stages of treatment: methanogenic anaerobic stage, anoxic stage and aerobic filtration stage with submerged ultrafiltration or microfiltration membranes. The anoxic and aerobic filtration stages combine the presence of biomass in suspension and biofilm adhered on a composite of plastic particles in suspension In the case of the aerobic filtration stage, the membrane is located in an area where there will be no plastic substrates. The appropriate combination of anaerobic, anoxic and aerobic membrane filtration treatment technologies in the same bioreactor can make the most of the advantages and strengths of each of the technologies such as the lower energy consumption and associated sludge production of anaerobic biological process, greater stability and less associated COD of treated water of aerobic processes, and the higher quality effluent with no suspended solids and microorganisms, associated with membrane filtration treatment and the possibility of eliminating nitrogen under anoxic conditions, avoiding the problems associated, separately, with each of these technologies. One of the main problems of anaerobic pre-treatment is the output of dissolved methane in the treated effluent, especially at low temperatures.

Wastewater is introduced into the methanogenic anaerobic chamber, where an important part of the wastewater COD is eliminated, generating a methane-rich biogas. The water leaving this stage, with less COD concentration, but saturated in methane, reaches the anoxic chamber, where microbial growth is promoted in suspension with the mixed liquor or adhered as a biofilm to the plastic substrate particles, where the fraction of residual COD and methane is removed as carbon sources for denitrifying the nitrate generated in stage 3. In the aerobic filtration stage the oxidation of ammonia to nitrite and/or nitrate is promoted, which is recirculated to the anoxic chamber where nitrogen removal occurs. Also in the aerobic filtration stage, the water is filtered by means of submerged membranes confined in an area free from plastic substrates by means of a perforated divider, producing a permeate with a COD of less than 40 mg/L, DBO5 of less than 5 mg/L, total nitrogen of less than 15 mg/L and free of suspended solids and microorganisms.

The use of a filtration membrane prevents the exit both of the anaerobic biomass washed from the first chamber, and the aerobic biomass that may become dislodged from the biofilm. This biomass can be recirculated to the anaerobic chamber, thus avoiding washing the anaerobic biomass and the loss of purification capacity of the chamber, observed in conventional methanogenic anaerobic systems for treating low load urban or industrial wastewater at low or warm temperatures. The recirculation of the aerobic biomass formed, into the anaerobic methanogenic chamber, means that at this stage there is also a digestion and stabilisation stage of the sludge in the aerobic chamber, slightly improving the production of biogas in the system and reducing the amount of sludge generated in the biological wastewater treatment process. Optionally the sludge from the anaerobic chamber may be purged and driven, together with excess biomass generated from the anaerobic stage, to a sludge management unit.

By using the anoxic and aerobic filtration stages, which promote the development of biomass adhered as biofilm to plastic substrate particles, substantially improves the removal of soluble or colloidal organic matter so as to prevent these compounds from reaching the area with filtration membranes and making contact with the membrane modules, thereby reducing fouling of the submerged membranes, allowing a more stable operation of the filtration units (Sanchez et al., Wat. Res., 47, 1227 (2013)). Thus the problems associated with the use of anaerobic membrane bioreactors are avoided, in which fouling of the membrane modules prevents achieving high flows (flow treated per square metre of membrane) and a high stability biological reactor is achieved where the membrane filtration modules can operate with the flows observed in aerobic membrane bioreactors, but without generating so much sludge or consuming as much energy as observed in such processes.

A notable additional advantage of the present invention is that in certain applications the biogas generated allows a significant portion of the energy required for the aeration of the aerobic biofilm filtration chamber and operation of the filtration membranes to be covered.

DESCRIPTION OF THE INVENTION

The present invention describes an anaerobic methanogenic reactor and membrane bioreactor for removing organic matter and nitrogen in wastewater. The system is especially useful for the biological treatment of urban or industrial wastewater with low or moderate concentrations of organic matter, preferably between 150 and 5,000 mg/L of organic matter, measured as COD, and especially allows the removal of 15 to 50 mg/L of total nitrogen present in wastewater. The system can operate at ambient temperature, and preferably at temperatures above 15° C.

In a first aspect, the invention relates to an integrated system of anaerobic methanogenic reactor and membrane bioreactor for removing organic matter and nitrogen in wastewater hereinafter, "the system of the invention", characterised in that it consists of three chambers:
an anaerobic methanogenic chamber (1),
an anoxic chamber (2) comprising a plastic filler particles in suspension (14a), and
an aerobic filter chamber (3) comprising a plastic filler particles in suspension (14b) and filtration membranes (20).

In FIGS. 1 and 2 the essential characteristics of the integrated system of anaerobic methanogenic reactor and membrane bioreactor are shown, while in FIGS. 3 and 4 certain essential design features of the invention are indicated.

In a preferred embodiment, the anaerobic methanogenic chamber (1) comprises: distribution boxes (4) with plastic tubing (5), one anaerobic sludge blanket (6), domes (7) and pipes (12) for the collection of biogas, deflectors (8), overflows (9), pump (10) for purging excess sludge and a cover (24). In a more preferred embodiment, the anaerobic sludge blanket (6) is located in the bottom of the anaerobic methanogenic chamber (1). In another more preferred embodiment, the domes (7) and pipes (12) for the collection of biogas are located at top of the anaerobic methanogenic chamber (1). In another more preferred embodiment, the deflectors (8) are located at the bottom of the anaerobic methanogenic chamber (1).

In the anaerobic methanogenic chamber (1) both the homogeneous distribution of the wastewater introduced into the bottom of the sludge blanket and the proper separation of biogas bubbles or suspended solids from the treated water should be promoted. To this end a number of elements are arranged inside said chamber: delivery boxes (4) with plastic tubing (5), anaerobic sludge blanket (6), preferably in the bottom of the reactor, domes (7) and pipes (12) for the collection of biogas, preferably at the top of the chamber, baffles (8), preferably installed on the bottom of the chamber, perimeter overflows (9), pump (10) for purging excess anaerobic sludge and a cover (24) to maintain odours confined that could be generated or emitted from the anaerobic methanogenic chamber (1).

The raw wastewater is fed to the first anaerobic methanogenic chamber (1) by gravity, or if the water levels so requires, using a pumping system (11), using the distribution boxes (4) located at the top of the chamber for this purpose. Therefore, in a more preferred embodiment, the anaerobic methanogenic chamber (1) further comprises a feed pump (11). A series of plastic hoses (5) emerge from the distribution box designed to introduce the wastewater entering at the bottom of the anaerobic sludge blanket (6). The wastewater flows upwards through the anaerobic sludge blanket. The anaerobic sludge blanket consists of anaerobic microorganisms that degrade the organic contaminants in the input wastewater, forming a biogas with high methane and carbon dioxide content. Biogas is collected using a set of domes (7), to which are connected pipes (12) to transport it to the biogas storage, energy recovery or incineration system installed for the proper management of the biogas produced. The deflector plates (8) used in the bottom of anaerobic methanogenic chamber (1) are used to guide some of the biogas formed in areas close to the plates, towards the collection domes (7), thus preventing the bubbles of biogas generated from freely leaving the chamber, together with the treated water.

The output of treated wastewater from the anaerobic chamber is performed through a series of overflows (9), preferably located at the top of the anaerobic methanogenic chamber (1) along the water surface, and establishing the maximum water level in the chamber. The function of these overflows is to promote the uniform rise of the water in the upper part of the chamber, avoiding the appearance of preferential flows, in a way that promotes the decanting of most of the sludge particles that have risen with the water to the top of the chamber. The anaerobic methanogenic chamber (1) will be equipped with a cover (24) to avoid the dispersion of odours in the environment, along with a conduit and pump used to purge the excess sludge (10) and maintain a stable level of the sludge blanket (6) in this chamber.

In another preferred embodiment, the anoxic chamber (2), in addition to the plastic filler particles in suspension (14a), comprises the following elements: a distribution system (13) consisting of perforated tubes, a tubular mesh (15a), a mechanical stirrer (22) and a pump (17). In another more preferred embodiment, the tubular mesh (15a) has a gauge smaller than the size of the plastic filler particles in suspension (14a) of the anoxic (2) camera. In another more preferred embodiment, the pump (17) is located between the anoxic (2) and the anaerobic methanogenic chamber (1). In another more preferred embodiment, the pump (17) is associated with any of the selected items from the list comprising: recirculation valve (25a) and purge valve (25b). In another more preferred embodiment, the bottom or hearth of the anoxic chamber has a slight incline, preferably a slope between 1/20 and 1/5 m/m. In another more preferred embodiment, the plastic filler particles in suspension (14a) of the anoxic chamber (2) consist of particles occupying between 10% and 60% of apparent volume of the anoxic chamber (2). In another more preferred embodiment, the plastic filler particles in suspension (14a) of the anoxic chamber (2) consist of an element selected from the list comprising: granular plastic particles of rough appearance, plastic Raschig rings, polymeric foam particles or similar commercial products to promote formation of microorganism biofilms. In another more preferred embodiment, the particles that make up the plastic filler particles in suspension (14a) of the anoxic chamber (2) have a size of between 1 and 5 mm.

Therefore, in a preferred embodiment, the anoxic chamber (2) is formed by the following elements: plastic filler particles in suspension (14a), distribution system (13), tubular mesh (15a) for extraction of water, mechanical stirrer (22) and recirculation pump (17) between the anoxic chamber (2) and the anaerobic methanogenic chamber (1). Water from the anaerobic methanogenic chamber (1) is brought into the anoxic chamber (2) using a distribution system (13) as shown in FIGS. 1 and 2 and said system is detailed in FIG. 3. Said distribution system is formed by a series of arms or parallel tubes provided with a row of holes at the bottom thereof, through which the wastewater is homogeneously distributed in the lower section of the anoxic chamber (2). The distribution system is preferably arranged in the lower part of the anoxic chamber (2), so that the net flow of wastewater occurs in an upward direction towards the top of the anoxic chamber (2) through the filler plastic particles (14a) and exiting through a tubular mesh (15a) for the removal of water, preferably arranged at the top of the system.

The filler consists of plastic particles (14a), of similar density to the water, which can move freely inside that chamber. In addition, the use of a mobile support of plastic particles limits the clogging or jamming of the filler layer owing to biomass accumulation, by promoting the balance between the processes of biofilm microbial growth and the dislodging of biomass from the filler. The filler can consist of granular plastic particles of rough appearance, plastic Raschig rings, commercial products such as Kaldnes K1, K2 or K3 rings by AnoxKaldnes (AnoxKaldnes Global AB, Sweden), Linpor type polymeric foam particles or any other similar plastic particle product that promotes the formation of a biofilm. The particle size of the filler is preferably between 1 and 5 mm.

In the anoxic chamber (2) the growth of heterotrophic bacteria in general is promoted and in particular methanotrophic bacteria, being present in suspension in the liquor mixture or adhered as biofilms to the plastic particles (14a), that oxidize both the biodegradable compounds and the dissolved methane present in the effluent of anaerobic methanogenic chamber (1), reducing the nitrates or nitrites formed in the aerobic filter chamber (3) to nitrogen gas which is then recirculated to the anoxic chamber (2). The ammonium from anaerobic methanogenic stage is hardly removed at all during this anoxic stage (2). In this way the invention ensures the efficient removal of nitrogen and soluble or colloidal biodegradable organic matter, thus reducing emissions of greenhouse gases associated with the degradation of dissolved methane.

In a preferred embodiment, the bottom or hearth of the anoxic chamber (2) has a mild to moderate slope, preferably an incline of between 1/20 and 1/5 m/m, and from the bottom emerges a conduit equipped with a pump (17) used to carry towards the anaerobic methanogenic chamber (1) both the anaerobic sludge that might have come from the chamber and the suspended sludge generated in the anoxic chamber (2) or aerobic filtration chamber (3), propelling the recirculated sludge through a conduit equipped with a recirculation valve (25a). This action prevents the washing of biomass from the anaerobic methanogenic chamber (1), as well as promoting the anaerobic digestion of the excess sludge formed in the anoxic chamber (2) and the aerobic filtration chamber (3). Alternatively, if necessary, that sludge can be purged via a conduit equipped with a purge valve (25b) fitted to propel the excess sludge generated the sludge management system of the treatment plant.

The mixture of treated wastewater with particles of biomass in suspension leaves the anoxic chamber (2) via a tubular mesh (15a) for the extraction of water, arranged at the top of the system and passes by gravity to the bottom of the aerobic filtration chamber (3). The mesh, with a gauge finer than the size of the support particles (and in any case always less than 5 mm) prevents the output of filler particles from the anoxic chamber (2).

In another preferred embodiment, the aerobic filtration chamber (3) is divided into two zones: a zone comprising a suspended plastic particle filler (14b) and another zone comprising filtration membranes (20), separated by a perforated partition (23) with holes with a diameter smaller than that of the suspended plastic particle filler (14b). In a more preferred embodiment, the zone comprising a suspended plastic particle filler (14b) of the aerobic filtration chamber (3), comprises, also: a system of air diffusers in a grate (18a), an air blower (19a), a tubular shaped mesh (15b) and a pump (16a), where the air blower (19a) blows air towards the system of air diffusers in a grate (18a). In another more preferred embodiment, the tubular shaped mesh (15b) has a span of less than the size of the particles that comprise the suspended plastic particle filler (14b) of the aerobic filtration chamber (3). In another more preferred embodiment, the suspended plastic particle filler (14b) of the aerobic filtration chamber (3) consists of particles that occupy from 10% to 60% of apparent volume of the aerobic filtration chamber (3). In another more preferred embodiment, the suspended plastic particle filler (14b) of the aerobic filtration chamber (3) consists of an element selected from the list comprising: granular plastic particles with a rough appearance, plastic Raschig rings, polymer foam particles or similar commercial products that promote the formation of biofilms of microorganisms. In another more preferred embodiment, the particles comprising the suspended plastic particle filler (14b) of the aerobic filtration chamber (3) have a size ranging from 1 to 5 mm. In another more preferred embodiment, the tubular shaped mesh (15b) is located at the top of the area with suspended plastic particle filler (14b) of the aerobic filtration chamber (3). In another more preferred embodiment, the zone comprising filtration membranes (20) of the aerobic filtration chamber (3) comprises: submerged microfiltration or ultrafiltration membrane modules (20), pumps (21) for extracting permeate, blower system (19b), and diffuser grate (18b). In another more preferred embodiment, the aerobic filtration chamber also comprises a pump (16b) between the zone with suspended plastic particle filler (14b) and the zone with filtration membranes (20).

Therefore, in a preferred embodiment, the aerobic filtration chamber (3) is made up of the following elements: plastic particle filler (14b), perforated partition (23), tubular mesh (15b) equipped with a pump (16a) to recirculate the mixed liquor mixture with nitrates to the anoxic chamber (2), internal recirculation pump (16b) between the zones with filtration membranes and the zone with plastic particle filler (14b) of the aerobic filtration chamber (3), modules of submerged microfiltration or ultrafiltration membrane (20) and its corresponding permeate pumps (21). In addition, and in the bottom of the zone with plastic particle filler (14b) it has an air diffuser in grate system (18a) and an air blower (19a). The zone with filtration membranes is equipped with an aeration system (18b) of the submerged membranes (20), using an additional blower (19b).

The filler of the aerobic filtration chamber is made up of plastic particles (14b), of identical characteristics to those outlined above for the plastic particle filler (14a) of the anoxic chamber. In a preferred embodiment, the apparent volume occupied by the plastic filler range from 10 to 60% of the volume of the zone with plastic particle filler (14b) of the aerobic filtration chamber (3). In another preferred embodiment, in the bottom part of the zone with plastic particle filler (14b) of the aerobic filtration chamber (3) an air diffuser grate (18a) is installed, which distributes the air supplied by the blower (19a) in order to transfer the oxygen required for biological degradation reactions and promote the movement of the bed of plastic particles, reserving some units of diffusers to avoid, also, the clogging of the metal tubular mesh (15b) with suspended solids (FIG. 4).

In the aerobic filtration chamber (3) growth of heterotrophic and autotrophic aerobic bacteria is promoted, both suspended in the mixed liquor and stuck to the plastic particle filler (14b), forming biofilms, that degrade the biodegradable compounds present in the effluent of the anoxic chamber (2) and oxidise the ammonia to nitrite and/or nitrate by aerobic nitrifying bacteria. In this way, elimination of biodegradable, soluble or colloidal organic matter and ammonia is guaranteed.

The liquor mixture passes from the zone with plastic particle filler to the zone with filtration membranes by a perforated partition (23) with a smaller span than the size of the filler plastic particles (14b) used. The mixture of wastewater treated with suspended biomass (suspended biomass (mixed liquor) is internally recirculated from the bottom of the zone with filtration membranes to the bottom part of the zone with plastic particle filler (14b) of the aerobic filtration chamber (3) by a pump (16b).

In a preferred embodiment, and in the zone with filtration membranes modules of microfiltration or ultrafiltration membrane modules (20) are installed, which can be made out of both hollow fibre and flat plate. From these membrane modules the treated wastewater is evacuated, free of suspended solids and microorganisms, through pipes and permeate pump(s) (21). These modules operate under the conditions specified by the manufacturer thereof and shall be equipped with auxiliary elements specified or recommended by it. In another preferred embodiment, diffusers with thick or thin bubbles are installed (18b) associated with blowers (19b) fitted below the membrane modules, to avoid or limit fouling of the same, according to the specifications of the supplier of the membrane. Part of the treated water will exit filtered and free of suspended solids, as permeate, through the membrane modules (20), while another part with concentrated suspended solids will return to the zone with plastic particle filler by a pump (16b) to favour the homogenisation between the two zones of the aerobic filtration chamber (3) and prevent the accumulation of suspended solids in the zone with filtration membranes. Part of the treated water with suspended solids is recirculated from the zone with plastic particle filler in the aerobic filtration chamber (3) towards the anoxic chamber (2), by a tubular mesh (15b) for water extraction equipped with a pump (16a), supplying the nitrate and/or nitrite necessary to eliminate nitrogen by biological denitrification reaction using as a carbon source mostly dissolved methane in the effluent of methanogenic anaerobic chamber (1) and avoiding accumulation of suspended solids in the aerobic filtration chamber (3).

The system of the invention is especially recommended for the treatment of wastewater with low concentrations of organic matter, preferably between 150 and 5000 mg/L COD. Between 60 and 85% of organic matter contained in the wastewater will be eliminated in the methanogenic anaerobic stage, producing a biogas containing 50-80% methane and 20-50% carbon dioxide or that is collected by the hoods (7) and the pipe system (12). The rest of the organic matter will be eliminated in the anoxic and aerobic filtration stages.

The system of the invention is also especially recommended for eliminating total nitrogen in wastewater, enabling an elimination of between 15 and 50 m/L of total nitrogen.

In another aspect, the invention relates to a method, hereinafter, "the method of the invention", for eliminating organic matter and nitrogen in wastewater with COD concentrations between 150 and 5000 mg/L by an integrated system of methanogenic anaerobic reactor and membrane bioreactor comprising three treatment stages: methanogenic anaerobic stage, anoxic stage with biofilms and suspended biomass and aerobic filtration stage with biofilms and suspended biomass, where the elimination of total nitrogen is between 15 and 50 mg/L.

In a preferred embodiment, the methanogenic anaerobic treatment stage occurs thanks to an anaerobic sludge blanket (6) arranged in a methanogenic anaerobic chamber (1), which degrades between 60 and 85% of organic matter contained in the wastewater, in terms of Chemical Oxygen Demand (COD), producing a biogas with a content of 50-80% of methane and 20-50% of carbon dioxide, which is collected by the hoods (7). In another preferred embodiment, in the methanogenic anaerobic treatment stage, the wastewater is introduced homogeneously through the bottom of the sludge blanket by a pump (11), using distribution boxes (4) and plastic hoses (5). In another preferred embodiment, the wastewater treated in the methanogenic anaerobic chamber (1) leaves it through overflows (9) placed along the surface of the sheet of water, and the sludge blanket level is controlled purging the sludge of said mantle through a pipe and a sludge purging pump (10).

In another preferred embodiment, the anoxic treatment stage is based on the use of heterotrophic anoxic microorganisms that grow suspended in the mixed liquor and attached, forming biofilms, a filler of plastic (14a) that are in an anoxic chamber (2) and that move thanks to a mechanical stirrer (22). In a more preferred embodiment, these microorganisms eliminate the biodegradable compounds which have not been eliminated during the methanogenic anaerobic treatment stage together with the dissolved methane in the effluent of said stage, employing them as a carbon source for denitrifying the nitrogen as nitrate or nitrite, which is recirculated from the aerobic filtration treatment stage. The use of mobile plastic particles limits the clogging of the filler as the detachment of the anoxic biomass generated in excess is promoted in them.

In another preferred embodiment, the aerobic filtration treatment stage is based on the use of heterotrophic and nitrifying aerobic microorganisms that grow in suspension in the mixed liquor and attached, forming biofilms, to the filler of plastic (14a) that are in the zone with filler of plastic particles of an aerobic filtration chamber. In a more preferred embodiment, said microorganisms will eliminate the biodegradable compounds that have not been eliminated during the methanogenic anaerobic or anoxic treatment stages and oxidise the ammonia from the anoxic treatment stage, transforming it into nitrate and/or nitrite. Both in the anoxic chamber (2) and in the aerobic filtration chamber (3) microorganisms are generated by biological degradation of organic contaminants and nitrogen ions within the biofilm or in the suspended sludge. The use of mobile plastic particles limits the clogging of the filler as the detachment of the excess aerobic biomass generated is promoted in them. In another preferred embodiment, the sludge with suspended solids generated returns from the zone with plastic particle filler (14b) from the aerobic filtration chamber to the anoxic chamber through a tubular shaped mesh (15a) for the extraction of water at the top of the anoxic chamber and a pump (16a). In another preferred embodiment, the aerobic filtration treatment stage, filtration is accomplished using submerged membrane modules (20) in a zone with filtration membranes, which is separated from the zone with a plastic particle filler (14b) thanks to a perforated partition (23), forming part of an aerobic filtration chamber. With these modules it is possible to obtain a treated water free of suspended solids and microorganisms, preventing both the sludge generated in excess during the anoxic and aerobic filtration stages and the anaerobic sludge that has been left by the methanogenic anaerobic treatment stage from exiting with the treated water. In another preferred embodiment, the sludge with suspended solids returns internally from the zone with filtration membranes area to the zone with plastic particle filler (14b) in the aerobic treatment stage by means of a pump (16b). In another preferred embodiment, the method also comprises the use of a recirculation system with a pump (17) and a recirculation valve (25a) installed in the anoxic chamber (2) so the sludge of the anaerobic sludge blanket (6) is returned of methanogenic anaerobic treatment stage which had migrated to the anoxic and aerobic stages of filtration and the anaerobic digestion of the sludge in excess is simultaneously promoted during the treatment stages in the anoxic chamber (2) and aerobic filtration chamber (3). The treatment capacity of the methanogenic aerobic stage is obtained using this pump and valve. In a more preferred embodiment, the pump (17) is also used to purge excess sludge through a purge valve (25b).

In another aspect, the invention relates to the use of the system and method of the invention as described above, for the treatment of organic matter and nitrogen in urban and/or industrial wastewater. In a preferred embodiment, said wastewater has concentrations of organic matter measured as COD, including, preferably between 150 and 5000 mg/L, and total nitrogen elimination that occurs is between 15 and 50 mg/L. In a preferred embodiment, said use preferably occurs at temperatures above 15° C.

Illustrative Embodiment

Treatment of urban wastewater produced in a population of 10,000 equivalent inhabitants, with a COD generation of 125 g, COD per equivalent inhabitant per day (or 60 g BOD5 per equivalent inhabitant per day), 10 g of total nitrogen (NT) per equivalent inhabitant per day and a generation of wastewater of 200 L per equivalent inhabitant per day, which will treat 1250 kg COD/d, 100 kg NT/d and 2500 m$^3$/d on average in dry weather.

An overall organic load speed of 1.0 kg COD/m$^3$/d is established, which is between 0.5 and 3 kg COD/m$^3$/d, under which the invention of the SIAM system could operate. The total volume of the biological reactor is 1250 m$^3$. The volume of the chambers is as follows: anaerobic chamber 812.5 m$^3$, anoxic chamber 250 m$^3$ and aerobic chamber and filtration chamber 187.5 m$^3$ of overall volume, wherein the volume is distributed as 65% for the anaerobic chamber, 20% for the anoxic chamber and 15% for the aerobic filtration chamber. The apparent support volume, used in the anoxic chamber, is around 125 m³ if a rigid plastic support is used or 50 m³ if polymer foam is used.

Between 60 and 85% of the biodegradable COD present in the inlet wastewater, is degraded in the methanogenic anaerobic chamber, and the remaining 15-40% is eliminated in the aerobic chamber or even in the membranes chamber. Sludge production is 150 kg TSS/d, the filtered effluent or permeate has COD lower than 40 mg/L, $BOD_5$ lower than 5 mg/L, eliminating between 15 and 50 mg/L of TN of the treated wastewater that is virtually free of suspended solids and microorganisms, facilitating even a potential reuse of the treated wastewater, while the membrane modules operate with flows equal to or higher than 15-20 L/m²/h.

Figure 1:
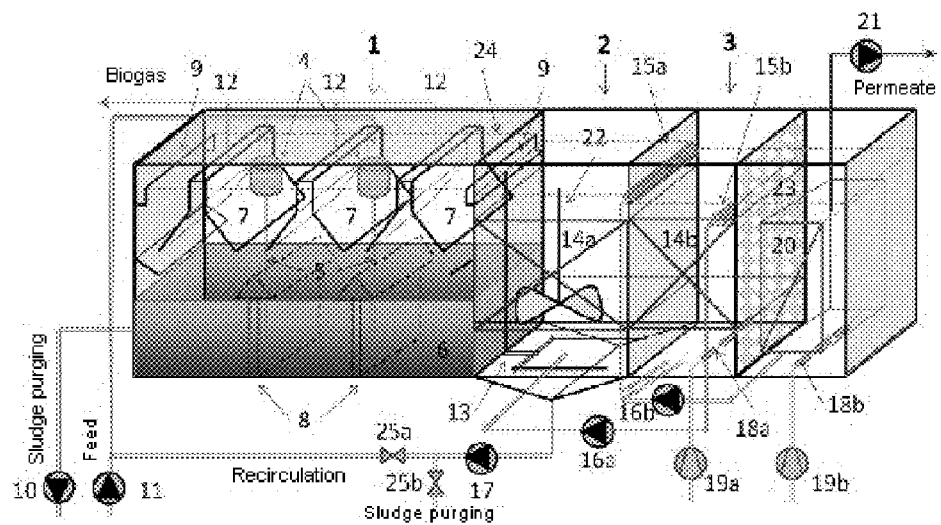
FIG. 1. Perspective in three dimensions of the Integrated System of methanogenic anaerobic reactor and membrane reactor (SIAM). The three chambers that make up the system: methanogenic anaerobic chamber (1), anoxic chamber (2) with suspended plastic particle filler (14a) and aerobic filtration chamber (3) with suspended plastic particle filler (14b) and submerged membrane modules (20). The aerobic filtration chamber (3) is divided into two zones, a zone where the suspended plastic particle filler (14b) is located and a zone where the filtration membranes (20) are located separated by a perforated partition (23).
Figure 2:
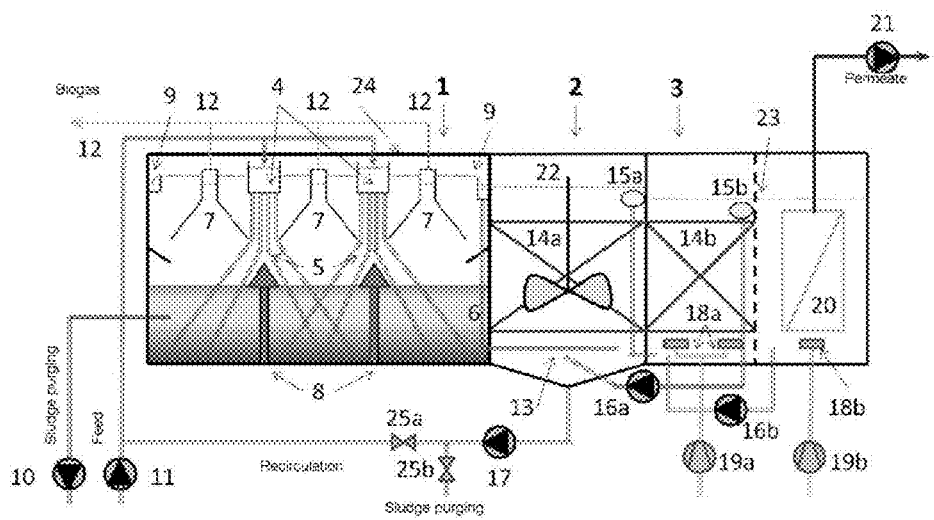
FIG. 2. Diagram of the integrated system where the three chambers can be seen: methanogenic anaerobic (1), anoxic (2) and aerobic filtration (3).
Figure 3:
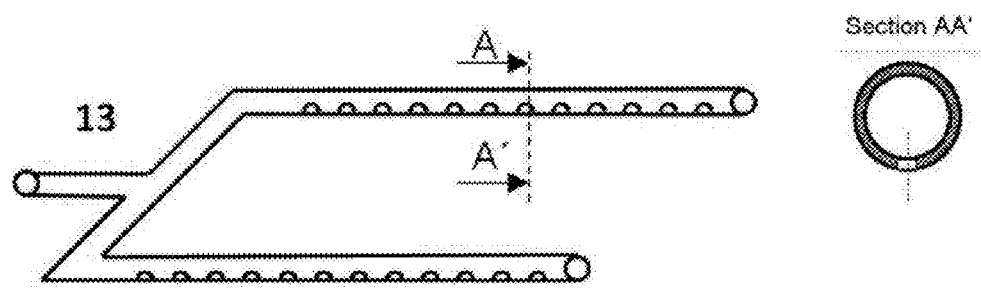
FIG. 3. Detail of the wastewater distribution system (13) used in the lower part of the anoxic chamber (2) and detail AA' of the cross section of one of the arms of the distribution system in which the section of the holes each arm consists of is observed.
Figure 4:
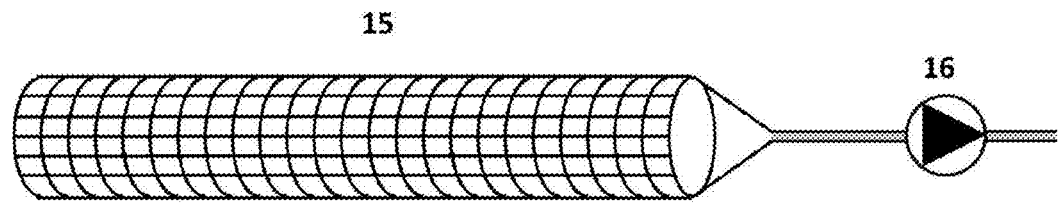
FIG. 4. Detail of the pipe formed by a tubular shaped mesh (15a, 15b) used to extract the water treated in the anoxic chamber (2) towards the aerobic filtration chamber (3) or to recirculate part of the treated water in the aerobic filtration chamber (3) to the anoxic chamber (2).

The invention claimed is:

1. An integrated methanogenic anaerobic reactor and membrane bioreactor system for the elimination of organic matter and nitrogen in wastewater comprising three chambers:
   a methanogenic anaerobic chamber;
   an anoxic chamber comprising a suspended plastic particle filler; and
   an aerobic filtration chamber comprising a suspended plastic particle filler and filtration membranes;
   wherein the anoxic chamber, in addition to the suspended plastic particle filler, comprises a distribution system formed by perforated tubes, a tubular shaped mesh, a mechanical stirrer and a pump.

2. The integrated system, according to claim 1, characterised in that the methanogenic anaerobic chamber comprises: distribution boxes with plastic tubing, an anaerobic sludge blanket, hoods and pipes for collection of biogas, deflectors, overflows, pump for purging excess sludge and a cover.

3. The integrated system according to claim 2, wherein the anaerobic sludge blanket is located in the bottom of methanogenic anaerobic chamber.

4. The integrated system, according to claim 1, wherein the tubular shaped mesh has a span of less than the size of the particles that form the suspended plastic particle filler.

5. The integrated system, according to claim 1, wherein the pump is located between the anoxic chamber and the methanogenic anaerobic chamber and is associated to any of the elements selected from the list that comprises: recirculation valve and purge valve.

6. The integrated system, according to claim 1, characterised in that the suspended plastic particle filler of the anoxic chamber comprises particles that occupy between 10% and 60% of the apparent volume of the anoxic chamber and in that the said plastic particle filler comprises: granular plastic particles with a rough appearance, plastic Raschig rings, polymer foam particles or similar commercial products that promote the formation of biofilms of microorganisms.

7. The integrated system according to claim 1, wherein the particles forming the suspended plastic particle filler of the anoxic chamber have a size between 1 and 5 mm.

8. The integrated system, according to claim 1, characterised in that the aerobic filtration chamber is divided into two zones: a zone comprising a suspended plastic particle filler and another zone comprising filtration membranes, separated by a perforated partition with holes with a diameter smaller than that of the suspended plastic particle filler.

9. The integrated system, according to claim 8, characterised in that the zone comprises a suspended plastic particle filler of the aerobic filtration chamber, further comprises: a system of air diffusers in a grate, an air blower, a tubular shaped mesh and a pump, where the air blower blows air towards the system of air diffusers in a grate.

10. The integrated system, according to claim 9, wherein the tubular shaped mesh has a span of less than the size of the particles that form the suspended plastic particle filler of the aerobic filtration chamber.

11. The integrated system, according to claim 8, wherein the zone that comprises filtration membranes of the aerobic filtration chamber comprises: submerged microfiltration or ultrafiltration membrane modules, pumps for extracting permeate, blower system, and diffuser grate.

12. The integrated system, according to claim 8, wherein the suspended plastic particle filler of the aerobic filtration chamber comprise particles that occupy between 10% and 60% of the apparent volume of the aerobic filtration chamber and comprises:
   granular plastic particles with a rough appearance, plastic Raschig rings, polymer foam particles or similar commercial products that promote the formation of biofilms of microorganisms.

13. A method for eliminating organic matter and nitrogen in wastewater with COD concentrations comprised between 150 and 5000 mg/L by an integrated system of methanogenic anaerobic reactor and membrane bioreactor comprising three treatment stages: methanogenic anaerobic stage, anoxic stage with biofilms and suspended biomass and aerobic filtration stage with biofilms and suspended biomass, where the elimination of total nitrogen is comprised between 15 and 50 mg/L;
   wherein the anoxic treatment stage is based on the use of heterotrophic anoxic microorganisms that grow suspended in the mixed liquor and attached, forming biofilms, a filler of plastic that are in an anoxic chamber and that move thanks to a mechanical stirrer, where said microorganisms eliminate the biodegradable compounds which have not been eliminated during the methanogenic anaerobic treatment stage together with the dissolved methane in the effluent of said stage, employing them as a carbon source for denitrifying the nitrogen as nitrate or nitrite, which is recirculated from the aerobic filtration treatment stage; and in that the aerobic filtration treatment stage is based on the use of heterotrophic and nitrifying aerobic microorganisms that grow in suspension in the mixed liquor and attached, forming biofilms, to the filler of plastic particles that are in the zone with filler of plastic particles of an aerobic filtration chamber.

14. The method, according to claim 13, characterised in that the methanogenic anaerobic treatment stage occurs thanks to an anaerobic sludge blanket arranged in a methanogenic anaerobic chamber, which degrades between 60 and 85% of organic matter contained in the wastewater, in terms of Chemical Oxygen Demand (COD), producing a biogas with a content of 50-80% of methane and 20-50% of carbon dioxide, which is collected by the hoods.

15. The method, according to claim 13, characterised in that in the methanogenic anaerobic treatment stage, the wastewater is introduced homogeneously through the bottom of the sludge blanket by a pump, using distribution boxes and plastic hoses; and in that the wastewater treated in the methanogenic anaerobic chamber leaves through overflows placed along the surface of the sheet of water, and the sludge blanket level is controlled purging the sludge through a pipe and a sludge purging pump.

16. The method, according to the claim 13, wherein the sludge with suspended solids generated returns from the zone with plastic particle filler from the aerobic filtration chamber to the anoxic chamber through a tubular shaped mesh for the extraction of water at the top of the anoxic chamber and a pump.

17. The method, according to claim 13, characterised in that the aerobic filtration treatment stage, filtration is accomplished using submerged membrane modules in a zone with filtration membranes, which is separated from the zone with a plastic particle filler thanks to a perforated partition, forming part of an aerobic filtration chamber.

18. A method for eliminating organic matter and nitrogen in wastewater with COD concentrations comprised between 150 and 5000 mg/L by an integrated system of methanogenic anaerobic reactor and membrane bioreactor comprising three treatment stages: methanogenic anaerobic stage, anoxic stage with biofilms and suspended biomass and aerobic filtration stage with biofilms and suspended biomass, where the elimination of total nitrogen is comprised between 15 and 50 mg/L;

wherein the system further comprises the use of a recirculation system with a pump and a recirculation valve installed in the anoxic chamber so the sludge of the anaerobic sludge blanket is returned of methanogenic anaerobic treatment stage which had migrated to the anoxic and aerobic stages of filtration and the anaerobic digestion of the sludge in excess is simultaneously promoted during the treatment stages in the anoxic chamber and aerobic filtration chamber.

* * * * *